United States Patent [19]

Ferlazzo et al.

[11] 4,025,549
[45] May 24, 1977

[54] PROCESS FOR PREPARING METHYL ACRYLATE OR MIXTURES THEREOF WITH ACRYLIC ACID

[75] Inventors: Natale Ferlazzo, Segrate (Milan); Gian Fausto Buzzi, Arona (Novara); Marcello Ghirga, Bresso (Milan); Benedetto Calcagno, Milan, all of Italy

[73] Assignee: Societa' Italiana Resine S.I.R. S.p.A., Milan, Italy

[22] Filed: Nov. 5, 1974

[21] Appl. No.: 521,101

[30] Foreign Application Priority Data

Nov. 28, 1973 Italy .................................. 31747/73

[52] U.S. Cl. .......................... 260/486 R; 252/458; 252/470
[51] Int. Cl.² ......................................... C07C 69/54
[58] Field of Search ................................ 260/486 R

[56] References Cited
UNITED STATES PATENTS

| | | | |
|---|---|---|---|
| 3,230,248 | 1/1966 | Yanagita et al. | 260/486 R |
| 3,819,685 | 6/1974 | Grasselli | 260/486 R |

Primary Examiner—Paul J. Killos
Attorney, Agent, or Firm—Sughrue, Rothwell, Mion, Zinn & Macpeak

[57] ABSTRACT

Methyl acrylate alone or in mixture with acrylic acid is prepared by passing a gaseous stream containing methanol, acrolein and oxygen at a velocity of 5 to 50 cm/sec through a fluidized catalytic bed formed of spherical particles 15 to 100 $\mu$ in size, said particles comprising from 10 to 80 wt.% silica support, the remainder consisting of an active catalytic component defined by one of the general formulae:

$$Mo_a V_b Me_c O_x$$

$$Mo_a W_d Me_c O_y$$

$$Mo_a V_b W_d Me_c O_z$$

wherein Me is Cr, Mn, Fe, Co, Ni, Cu, Zn, Ag, Cd, Au, Hg, Na, Ba, Ca, Ce, Bi, Th, U, Pb, Sb, Sn, P or B; and wherein $a$ is a number from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5.

30 Claims, No Drawings

PROCESS FOR PREPARING METHYL ACRYLATE OR MIXTURES THEREOF WITH ACRYLIC ACID

The invention relates to an improved process for preparing methyl acrylate or a mixture thereof with acrylic acid.

The methyl ester of acrylic acid is a valuable product, which is employed more particularly in preparing widely used polymeric products. Acrylic acid is also largely employed in the art.

Various processes are known for preparing esters of acrylic acid, such as those based on hydrolysis of acrylonitrile or reaction of acetylene, carbon monoxide and an alcohol in the presence of a nickel carbonyl complex.

According to a process which is largely employed in industry, propylene is oxidized to acrolein on a suitable oxidation catalyst, the resulting acrolein being catalytically oxidized to acrylic acid. The acid is then esterified by reaction with a lower aliphatic alcohol at a further reaction step.

The above-described process is rather complex in that it comprises multiple reaction steps which entail expensive purification and recycle treatments.

Moreover, the overall acrylic esters output is relatively low.

According to a further known process, propylene is directly oxidized to acrylic acid on a suitable catalyst in a single reaction step. With this process the propylene conversion to acrylic acid is generally very low, large quantities of unsaturated aldehyde mixed with the unsaturated carboxylic acid being further produced. This necessitates the separation of the unsaturated aldehyde and unaltered propylene from the reaction products, as well as the purification and recycle of such products with inherent disadvantages.

According to our prior U.S. patent application Ser. No. 469,446 filed May 13, 1974 the methyl ester of acrylic acid is prepared by contacting a gaseous flow comprising acrolein, oxygen and methanol with a special catalyst. This considerably simplifies the process for the preparation of the methyl ester of acrylic acid.

Moreover, according to the said patent application, acrylic acid can be produced at the same time as methyl acrylate. The process is so flexible that the ratio of acrylic acid to its corresponding methyl ester in the reaction products can be adjusted simply by varying the acrolein/methanol ratio in the gaseous feed to the catalyst. Suitable catalysts for such conversion are oxides of molybdenum, vanadium and/or tungsten, possibly in combination with further metal oxides.

The present invention affords considerable improvements in the preparation of methyl acrylate or mixtures thereof with acrylic acid by the process (oxyesterification process) wherein a gaseous flow containing acrolein, oxygen and methanol is contacted with the above described catalysts (oxyesterification catalysts). The improvements reside more particularly in the properties conferred to the catalyst, making it highly active and suitable for use in the form of fluidized bed during commercially useful periods of time.

Thus, the present invention provides a process for preparing methyl acrylate or a mixture of methyl acrylate and acrylic acid by contacting with a catalyst a reacting gaseous flow containing methanol, acrolein and oxygen, characterized in that the reacting gaseous flow is led at a velocity of 5 to 50 cm/sec through the fluidized catalyst formed of regular spherical particles 15 to 100 microns in size, the said particles comprising from 10 to 80 wt.% of a silica support, the remainder consisting of an active component defined by one of the following general formulae:

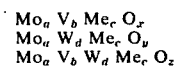

wherein Me stands for: chromium, manganese, iron, cobalt, nickel, copper, zinc, silver, cadmium, gold, mercury, sodium, barium, calcium, cerium, bismuth, thorium, uranium, lead, antimony, tin, phosphorus and boron; and wherein $a, b, c, d, x, y$ and $z$ are respectively: $a$ from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5. The said catalyst can be prepared in various manners.

A first procedure comprises the steps of preparing an ammoniacal aqueous solution of soluble compounds of the metals present in the said active component, such as ammonium paramolybdate, ammonium metavanadate, ammonium tungstate, tungstic acid, copper nitrate, copper acetate, zinc nitrate, ferric nitrate and ferrous oxalate, the resulting solution being admixed with a soluble silicate such as ammonium silicate. Useful products for the purpose are those known as soluble silica or ammoniacal soluble silica such as the product known under the trade name "Ludox AS".

Favourable results are obtained with aqueous solutions having a content of said compounds up to 10–12% by weight. The resulting solution is sprayed in droplet form into contact with a gas such as air, supplied at a temperature from 350° to 450° C in co-current or countercurrent flow to the droplets so as to evaporate water. Apparatus such as spray-drier, prilling tower or similar can be employed for the purpose.

The resulting solids are in the form of tough microspheroidal particles and are heated in an air stream at a temperature from 150° to 350° during a period from 0.1 to 4.0 hours, subsequently in an inert atmosphere, generally in nitrogen, at a temperature from 350° to 480° C during a period of 0.5 to 14 hours.

When air is employed for evaporating water from the solution, the resulting solids can be directly treated in a nitrogen atmosphere, thereby dispensing from the heat treatment in air.

The catalyst can also be prepared by impregnation of microspheroidal silica with one or more aqueous solutions of compounds of the catalytic metals present in the said active component. To this end silica is conveniently used in the form of particles 15 to 100 microns in size exhibiting the following ranges of properties: specific surface area 20 to 700 sq.m/g, pore volume 0.5 to 2 ml/g, density 0.25–1 g/ml.

The impregnated product is dried at a temperature up to 120° C.

The impregnation and drying treatments can be repeated several times till the proportion of said compounds of the metals on the support is in the desired range of values. This is followed by heat treatment in air, subsequently in an inert atmosphere in the manner described above.

The catalyst is obtained in the form spherical particles 15 to 100 microns in size, having a preferred bulk density from 0.5 to 1.2 g/ml. This catalyst is active and selective in the preparation of methyl acrylate or a mixture thereof with acrylic acid starting from acrolein, oxygen and methanol. The said catalyst is moreover easily fluidized and exhibit high mechanical properties so that crumbling and pulverizing are minimized. The catalyst is therefore suitable for use during commercially useful periods.

Conveniently, the gaseous flow contacted with the catalyst contains from 1 to 8% by volume acrolein, 0.5 to 20% by volume oxygen and 0.5 to 10% by volume methanol, the remaining percentage consisting substantially of inert gases such as nitrogen, carbon dioxide and steam. It is moreover convenient to maintain an acrolein/oxygen molar ratio from 0.1:1 to 4:1 (the preferred range being from 0.2:1 to 2:1) and an acrolein/methanol ratio from 0.2:1 to 4:1 (the preferred range being from 0.3:1 to 3:1).

The gaseous flow is preferably led through the fluidized catalyst bed at velocity from 10 to 40 cm/sec. The temperature is advantageously from 180° to 320° C, preferably from 220° to 280° C, the contact period being conveniently from 0.1 to 40 sec, preferably from 1 to 20 sec. It is moreover possible to operate at atmospheric pressure or slightly superatmospheric pressure such as up to 5 kg/sq cm.

Under these conditions useful reaction products (methyl acrylate, acrylic acid) are obtained with a selectivity amounting to 90% at least with respect to the converted acrolein, said conversion amounting to 95% at least.

According to an embodiment of the process of the invention, the aforesaid catalyst is contacted with said gaseous flow comprising the gases obtained in the catalytic oxidation of propylene to acrolein, said gases being previously admixed with methanol and possibly with oxygen and/or an inert gas such as steam.

Thus, in a first step (oxidation step), a conversion of propylene to acrolein is essentially effected, and in a second step (oxyesterification step), the conversion of acrolein to methyl acrylate and also to acrylic acid is effected in the manner previously described.

Catalysts useful for the oxidation of propylene are those known in the art, as cuprous oxide, mixed oxides of bismuth and molybdenum or cobalt and antimony oxide combined with further metal oxides.

Further useful propylene oxidation catalysts are combinations of oxides comprising tungsten oxide, or silver selenite activated with cuprous oxide, or cobalt molybdate in combination with tellurium oxide. These catalysts can be employed in the form of a stationary, fluidized or movable bed, though the fluidized bed technique is preferred.

Typically, the oxidation catalyst is supplied with a gaseous stream containing 1 to 8% by volume propylene and 4 to 20% by volume oxygen, th remaining percentage being formed of inert gases such as nitrogen, carbon dioxide or steam.

More particularly, in the gaseous stream a propylene/oxygen molar ratio from 0.2:1 to 1:1 is maintained, the preferred range being from 0.3:1 to 0.6:1. The temperature is from 300° to 400° C, preferably from 330° to 370° C and the contact period under reaction conditions is from 1 to 20 seconds, preferably from 2 to 6 seconds. Finally, the oxidation step can be carried out at atmospheric pressure or slightly above the atmospheric pressure, such as up to 3 kg/sq. cm.

By proceeding under the above conditions a propylene conversion of 95 to 98% with respect to the feed is normally obtained, the selectivity for acrolein being from 85 to 90% with respect to the reacted propylene.

The gaseous flow discharged from the first step is then enriched with methanol and possibly oxygen and/or an inert gas to obtain the hereinbefore-defined reacting gaseous flow suitable for the subsequent oxyesterification step.

Combination of the two steps is particularly favourable, inasmuch as any traces of removed oxydation catalyst do not deposit on the oxyesterification catalyst, but are carried along by the gaseous stream.

This is believed to be attributable to the peculiar physical form of the oxyesterification catalyst as well as to the operational conditions during the oxyesterification step. At any rate by proceeding as described poisoning of the second step catalyst is avoided, whereby the process is suitable for commercial exploitation.

Finally, methyl acrylate and acrylic acid are recovered from the stream issuing from the oxyesterification zone by any method known in the art. For instance, the gases can be absorbed by bubbling and extraction in water followed by distillation.

The following experimental examples further illustrate the invention.

EXAMPLE 1

60 liters water are charged into an enamelled 200 liter boiler heated by steam flowing in an outer jacket. The temperature is raised to 90° C and 2,430 g ammonium paramolybdate: $(NH_4)_6Mo_7O_{24}\cdot 4H_2O$ and subsequently 602.5 g ammonium metavanadate: $NH_4VO_3$ are dissolved while stirring.

354 g tungstic acid $H_2WO_4$ are separately dissolved in an ammoniacal aqueous solution formed by 5 liters water and one liter 28% by weight aqueous ammonia. The second solution is poured into the former and the whole concentrated during six hours at 90° C to a residual solution of 30 liters, then cooled and admixed with a solution of 1,728 g copper nitrate $Cu(NO_3)_2\cdot 3H_2O$ in 7 liters water.

The resulting solution is admixed with 2.5 liters 28% by weight aqueous ammonia, stirring being continued during a few minutes whereupon 4.2 liters silica hydrosol, known under the trade name Ludox AS containing 30% silica by weight, diluted with four liters water are added.

The resulting solution is stirred during a few minutes then centrifugally sprayed in co-current with air heated at 400° C.

A micro-spheroidal solid particulate product 20–100 microns in size is obtained and is maintained during two hours at 300° C in an air stream and during 2 hours at 390° C in a bed fluidized with nitrogen.

The resulting catalyst has a specific surface area of 23 sq.m/g and a bulk density of 1.1g/ml.

EXAMPLE 2

Two stainless steel AISI 316 reactors of vertically elongated tubular form and 60 mm in bore diameter are used in series.

The first reactor is charged with 1.5 liter of a known catalyst for oxidizing propylene to acrolein, formed of bismuth phosphomolybdate particles 30 to 80 microns in size.

The second reactor is charged with 1.5 liter catalyst prepared as described in Example 1. The first reactor is operated with the oxidation catalyst in the form of a fluidized bed, the reactor being fed at the bottom at a rate of 584 liters/hr (measured at 20° C and ambient pressure) with a gaseous mixture containing 4.0% by volume propylene, 10.5% by volume oxygen, 4.0% by volume steam, the remaining percentage being nitrogen.

The first reactor is operated at a temperature of 350° C. with a contact period of 4 sec under reaction conditions, the resulting propylene conversion amounting to 95%, the selectivity for acrolein and acrylic acid being 90% with respect to the reacted propylene.

The stream issuing from the top of the first reactor is admixed with gaseous methanol to obtain a gaseous flow of the following composition by volume: 0.2% propylene, 3.2% acrolein, 1.2% CO and $CO_2$, 0.4% acrylic acid, 4.8% oxygen, 8.3% steam, 1.2% methanol, the remainder being nitrogen.

The said gaseous flow is fed at the bottom of the second reactor which is operated with a fluidized catalytic bed at a temperature of 258° C. The velocity of the said gaseous flow is of 10.3 m/sec and the contact time is of 4.8 seconds.

The gases issuing from the top of the second reactor are submitted to gas-chromatographic analysis. The acrolein conversion amounts to 95.6%, the selectivity for methyl acrylate and acrylic acid with respect to converted acrolein amounting to 97.4%.

The methyl acrylate yield with respect to the methanol feed amounts to 70%.

EXAMPLE 3

The catalyst support employed is a micro-spheroidal commercial silica of the following properties:
specific surface area; about 600 sq.m/g
pore volume; about 1.1 ml/g
bulk density; about 0.45 g./ml
$SiO_2$ content; above 99.5%
$Al_2O_3$ content; less than 0.3%
$Na_2O$ content; less than 0.03%
Fe content; less than 0.03%

Moreover 80–90% particles of the said silica are 30 to 100 microns in size, the remainder being from 15 to 30 microns in size.

2,370 g of the described silica are impregnated at room temperature with an aqueous solution containing 315 g copper nitrate $Cu(NO_3)_2 \cdot 3H_2O$ dissolved in 2,100 ml water, then dried in an oven during two hours at 120° C.

An aqueous solution of the molybdenum, vanadium and tungsten salts is prepared in the manner described in Example 1, from 810 g ammonium paramolybdate, 210 g ammonium metavanadate and 118g tungstic acid in 10 liters water.

The support previously treated with the copper nitrate solution is impregnated at 80° C with the resulting solution concentrated to a volume of 2.1 liters, then dried during two hours at 120° C and treated during two hours at 300° C in an air stream and during two hours at 400° C in a nitrogen stream. The resulting catalyst is of a bulk density of 0.63 g/ml.

EXAMPLE 4

This embodiment comprises two reaction steps in series, in the first of which propylene is oxidized to acrolein in exactly the same manner as described in Example 2, yielding at the top of a first reactor a gaseous stream consisting of 0.2% propylene, 3.2% acrolein, 0.4% acrylic acid, 4.8% oxygen, 8.3% steam, 1.2% CO and $CO_2$ by volume, the remainder being nitrogen.

This stream is admixed with methanol in a proportion of 1.2% by volume, then with steam in a proportion of 8% by volume of the total resulting mixture.

The gaseous mixture is then fed at the bottom of an AISI 316 stainless steel vertical tubular reactor 60 mm in bore diameter, containing two liters of the catalyst prepared as described in Example 3. The second reactor is operated with the fluidized catalyst at a temperature of 258° C. The velocity of the gaseous mixture is of 11.4 m/sec and the contact time is of 4.3 seconds.

The gases issuing at the top of the second reactor are submitted to gas-chromatographic analysis. The acrolein conversion determined amounts to 97.8%, the selectivity for methyl acrylate and acrylic acid amounting to 95% with respect to the converted acrolein.

The methyl acrylate yield with respect to the methanol feed amounts to 66%.

When operating under the above-described conditions, by lowering the temperature in the second reactor and adjusting it to 235° C, an acrolein conversion of 96% and a selectivity for methyl acrylate and acrylic acid of 96% with respect to the converted acrolein are ascertained. Moreover the methyl acrylate yield with respect to the methanol feed amounts to 74%.

We claim:
1. A method for preparing methyl acrylate or a mixture of methyl acrylate and acrylic acid by contacting with a catalyst a reacting gaseous flow comprising methanol, acrolein and oxygen, which comprises passing the said gaseous flow at a velocity of 5 to 50 cm/sec through a fluidized catalyst bed formed of regular spherical particles 15 to 100 microns in size, said particles comprising 10 to 80 Wt.% of a silica support, the remainder consisting of an active catalytic component chosen in the group of components defined by the general formulae:

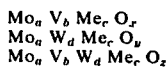

$$Mo_a V_b Me_c O_x$$
$$Mo_a W_d Me_c O_y$$
$$Mo_a V_b W_d Me_c O_z$$

wherein Me is an element chosen in the group consisting of chromium, manganese, iron, cobalt, nickel, copper, zinc, silver, cadmium, gold, mercury, sodium, barium, calcium, cerium, bismuth, thorium, uranium, lead, antimony, tin, phosphorus aand boron; and wherein $a$, $b$, $c$, $d$, $x$, $y$, $z$ are numbers varying respectively: $a$ from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5, said catalyst having been obtained by forming an ammoniacal aqueous solution of soluble silicate and of compounds of the elements other than oxygen present in the said active component, at a concentration of the said compounds up to 10–12 wt.% in the solution, spray-drying said solution with a gas at a temperature from 350° to 450° C and maintaining the resulting particulate solid product in an air stream during 0.1 to 4 hours at a temperature from 150° to 350° C and subsequently in an inert gas stream during 0.5 to 14 hours at a temperature from 350° to 480° C.

2. The method of claim 1, wherein the catalyst has a bulk density from 0.5 to 1.2 g/ml.

3. The method of claim 1, wherein the said gaseous flow comprises from 1 to 8 vol % acrolein, from 0.5 to 20 vol.% oxygen and from 0.5 to 10 vol % methanol, the remaining part consisting substantially of inert gases.

4. The method of claim 1, wherein the molar ratio of acrolein to oxygen in the said gaseous flow is from 0.1:1 to 4:1 and the molar ratio of acrolein to methanol from 0.2:1 to 4:1.

5. The method of claim 4, wherein the molar ratio of acrolein to oxygen is from 0.2:1 to 2:1 and the molar ratio of acrolein to methanol from 0.3:1 to 3:1.

6. The method of claim 1, wherein the temperature is from 180 to 320 C and the contact period from 0.1 to 40 sec.

7. The method of claim 1, wherein the temperature is from 220 to 280 C and the contact period from 1 to 20 sec.

8. The method of claim 1, wherein the said gaseous flow comprises the gases obtained in the catalytic oxidation of propylene to acrolein.

9. The method of claim 3, wherein the said gaseous flow comprises the gases obtained in the catalytic oxidation of propylene to acrolein.

10. The method of claim 8, wherein the said gaseous flow consists substantially of the said gases admixed with methanol.

11. The method of claim 8, wherein the said gaseous flow consists substantially of the said gases admixed with methanol and an inert gas.

12. The method of claim 8, wherein the said gaseous flow consists substantially of the said gases admixed with methanol and oxygen.

13. The method of claim 8, wherein the said gaseous flow consists substantially of the said gases admixed with methanol, oxygen and an inert gas.

14. The method of claim 1, wherein the said catalyst having a bulk density from 0.5 to 1.2 g/ml is contacted with the said gaseous flow comprising 1 to 8 vol % acrolein, 0.5 to 20 vol % oxygen and 0.5 to 10% methanol, the remainder of said flow consisting substantially of inert gases, the molar ratio of acrolein to oxygen in the said gaseous flow being from 0.1:1 to 4:1 and the molar ratio of acrolein to methanol from 0.2:1 to 4:1, the contact time being from 0.1 to 40 seconds and the temperature from 180 to 320 C.

15. The method of claim 14, wherein the said gaseous flow comprises the gases obtained in the catalytic oxidation of propylene to acrolein.

16. A method for preparing methyl acrylate or a mixture of methyl acrylate and acrylic acid by contacting with a catalyst a reacting gaseous flow comprising methanol, acrolein and oxygen, which comprises passing the said gaseous flow at a velocity of 5 to 50 cm/sec through a fluidized catalyst bed formed of regular spherical particles 15 to 100 microns in size, said particles comprising 10 to 80 wt.% of a silica support, the remainder consisting of an active catalytic component chosen in the group of components defined by the general formulae:

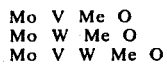

wherein Me is an element chosen in the group consisting of chromium, manganese, iron, cobalt, nickel, copper, zinc, silver, cadmium, gold, mercury, sodium, barium, calcium, cerium, bismuth, thorium, uranium, lead, antimony, tin, phosphorus and boron; and wherein $a$, $b$, $c$, $d$, $x$, $y$, $z$ are numbers varying respectively: $a$ from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5, said catalyst having been obtained by impregnating silica particles 15 to 100 microns in size with an aqueous solution of compounds of the elements other than oxygen present in the said active component, drying said impregnated particles at a temperature up to 120 C and treating the dried particles during 0.1 to 4 hours in an air stream at a temperature from 150 C to 350 C then during 0.5 to 14 hours in an inert gas stream at a temperature from 350 C to 480 C.

17. The method of claim 16, wherein the catalyst has a bulk density from 0.5 to 1.2 g/ml.

18. The method of claim 16, wherein the said gaseous flow comprises from 1 to 8 vol % acrolein, from 0.5 to 20 vol. % oxygen and from 0.5 to 10 vol % methanol, the remaining part consisting substantially of inert gases.

19. The method of claim 16, wherein the molar ratio of acrolein to oxygen in the said gaseous flow is from 0.1:1 to 4:1 and the molar ratio of acrolein to methanol from 0.2:1 to 4:1.

20. The method of claim 19, wherein the molar ratio of acrolein to oxygen is from 0.2:1 to 2:1 and the molar ratio of acrolein to methanol from 0.3:1 to 3:1.

21. The method of claim 16, wherein the temperature is from 180 to 320 C and the contact period from 0.1 to 40 sec.

22. The method of claim 16, wherein the temperature is from 220 to 280 C and the contact period from 1 to 20 sec.

23. The method of claim 16, wherein the said gaseous flow comprises the gases obtained in the catalytic oxidation of propylene to acrolein.

24. The method of claim 18, wherein the said gaseous flow comprises the gases obtained in the catalytic oxidation of propylene to acrolein.

25. The method of claim 23, wherein the said gaseous flow consists substantially of the said gases admixed with methanol.

26. The method of claim 23, wherein the said gaseous flow consists substantially of the said gases admixed with methanol and an inert gas.

27. The method of claim 23, wherein the said gaseous flow consists substantially of the said gases admixed with methanol and oxygen.

28. The method of claim 23, wherein the said gaseous flow consists substantially of the said gases admixed with methanol, oxygen and an inert gas.

29. The method of claim 16, wherein the said catalyst having a bulk density from 0.5 to 1.2 g/ml is contacted with the said gaseous flow comprising 1 to 8 vol % acrolein, 0.5 to 20 vol % oxygen and 0.5 to 10% methanol, the remainder of said flow consisting substantially of inert gases, the molar ratio of acrolein to oxygen in the said gaseous flow being from 0.1:1 to 4:1 and the molar ratio of acrolein to methanol from 0.2:1 to 4:1, the contact time being from 0.1 to 40 seconds and the temperature from 180 to 320° C.

30. The method of claim 29, wherein the said gaseous flow comprises the gases obtained in the catalytic oxidation of propylene to acrolein.

* * * * *